US006492178B1

(12) United States Patent
Pandian

(10) Patent No.: US 6,492,178 B1
(45) Date of Patent: Dec. 10, 2002

(54) METHODS OF DETERMINING AN INCREASED RISK OF A WOMAN CARRYING A DOWNS SYNDROME AFFECTED FETUS BY MEASURING AN ANALYTE IN A BIOLOGICAL SAMPLE

(75) Inventor: Murugan R. Pandian, Mission Viejo, CA (US)

(73) Assignee: Quest Diagnostic Investments, Incorporated, Wilmington, DE (US)

( * ) Notice: Subject to any disclaimer, the term of this patent is extended or adjusted under 35 U.S.C. 154(b) by 8 days.

(21) Appl. No.: 09/634,118

(22) Filed: Aug. 8, 2000

Related U.S. Application Data

(62) Division of application No. 09/229,136, filed on Jan. 12, 1999, now Pat. No. 6,127,186.

(51) Int. Cl.$^7$ .................. G01N 33/48; G01N 33/00; G01N 33/53; G01N 33/573; C12Q 1/00
(52) U.S. Cl. ................. 436/65; 436/86; 436/87; 436/814; 436/817; 436/818; 436/510; 435/4; 435/7.1; 435/7.4; 435/21
(58) Field of Search ............. 436/65, 86, 87, 436/814, 817, 818, 510; 435/4, 7.1, 7.4, 21

(56) References Cited

PUBLICATIONS

Raty et al. , "Prediction of pre–eclampsia with maternal mid–trimester total renin, inhibin A, AFP and free. beta.–hCG levels." Prenatal Diagnosis, (1999) 19/2 (122–27)–abstract.*
Weinans et al., "Urinary hyperglycosylated hCG in first trimester screening for chromosomal abnormalities", *Prenatal Diagnosis*, 2000, 20:976–978.
Cole et al., "Combining β–core fragment and total oestriol measurements to test for Down syndrome pregnancies", *Prenatal Diagnosis*, 1997, 17:12: 1125–1133.
Cole et al., "Screening for Down syndrome using urine hCG free β–subunit in the second trimester of pregnancy", *Prenatal Diagnosis*, 1997, 17:12: 1107–1111.
Hallahan et al., "Comparison of Urinary free beta (hCG) and beta–core (hCG) in prenatal screening for chromosomal abnormalities", *Prenatal Diagnosis*, 1998, 18: 893–900.

Hsueh et al., "Human prorenin", *Hypertension*, 1991, 17: 469.
Derkx et al., "Immunoreactive renin, proprenin and enzymatically active renin in plasma during pregnancy and in women taking oral contraceptives", *J. Clin. Endocrinol. Metab.*, 1986, 63: 1008.
Sealey, "Plasma renin activity and plasma prorenin assays", *Clin. Chem.*, 1991, 37:10(B), 1811–1819.
Heusser et al., "Monoclonal antibodies to human renin: properties and applications", *Clin. Exper. Theory Practice*, 1987: A9(8&9): 1259–1275.
Zuo et al., "Characterization of a monoclonal antibody specific for human active renin", *Hypertension*, 1992, 19:249–254.
Simon et al., "Two–site direct immunoassay specific for active renin", *Clin. Chem.*, 1992, 38/10: 1959–1962.
Rodbard et al., "Statistical analysis of radioimmunoassays and related procedures in medicine", *International Atomic Energy Agency, Vienna*, 1994, vol. 1.
Bogart et al., "Abnormal maternal serum chorionic gonadotropin levels in pregnancies with fetal chromosome abnormalities", *Prenatal Diagnosis*, 1987, 7: 623–630.
Brambati et al., "Serum PAPP–A free β–hCG are first–trimester screening markers for down syndrome", *Prenatal Diagnosis*, 1994, 14: 1043–1047.
Cole et al., "Comparison of 12 assays for detecting hCG and related molecules in urine samples from down syndrome pregnancies", *Prenatal Diagnosis*, 1997, 17:7: 607–614.
Crandall et al., "First–trimester maternal serum unconjugated oestriol and alpha–fetoprotein in fetal down's syndrome", *Prenatal Diagnosis*, 1991 11: 377–380.
Kratzer et al., "First–trimester aneuploidy screening using serum human chorionic gonadotropin (hCG), free ahCG, and progesterone", *Prenatal Diagnosis*, 1991 11:751–765.
Norton et al., "Maternal serum CA 125 for aneuploidy detection in early pregnancy", *Prenatal Diagnosis*, 1992 12: 779–781.

\* cited by examiner

*Primary Examiner*—Jill Warden
*Assistant Examiner*—Monique T. Cole
(74) *Attorney, Agent, or Firm*—Stout, Uxa, Buyan & Mullins, LLP; Donald E. Stout; Geg Hollrigel

(57) ABSTRACT

There are provided methods for assaying biological specimens for one or more of leptin, prorenin or renin in order to provide predictive information about the likelihood of a woman carrying a Downs Syndrome affected fetus.

16 Claims, No Drawings

METHODS OF DETERMINING AN INCREASED RISK OF A WOMAN CARRYING A DOWNS SYNDROME AFFECTED FETUS BY MEASURING AN ANALYTE IN A BIOLOGICAL SAMPLE

This application is a divisional application of U.S. Ser. No. 09/229,136, filed Jan. 12, 1999, now U.S. Pat. No. 6,127,186.

FIELD OF THE INVENTION

The present invention relates to assay methods which allow for the detection, and quantitation, of analytes; such as, leptin and/or prorenin and/or renin, in biological samples, such as blood or urine from a pregnant woman, which are associated with an increased risk that the pregnant woman's fetus has Downs Syndrome.

BACKGROUND OF THE INVENTION

Trisomy 21, commonly known as Downs syndrome, is characterized by an extra copy of chromosome 21. People afflicted with Downs syndrome have severe mental retardation, reduced life expectancies, and abnormal immune responses that predispose them to serious infections as well as thyroid autoimmunity. Further, 40% of Downs syndrome patients have congenital heart disease and a 10 to 20-fold increased risk of developing leukemia relative to the general population. All Downs syndrome patients older than 40 develop neuropathological changes characteristic of Alzheimer's disease.

Prenatal tests to detect aneuploidy, such as trisomy 21, by amniocentesis or chorionic villus sampling (CVS) have been available since the late 1960s. Amniocentesis is the most common invasive prenatal diagnostic procedure. In amniocentesis, amniotic fluid is sampled by inserting a hollow needle through the mother's anterior abdominal and uterine walls into the amniotic cavity by piercing the chorion and amnion. It is usually performed in the second trimester of pregnancy. CVS is performed primarily during the first trimester, and involves collecting cells from the chorion which develops into the placenta.

Another invasive prenatal diagnostic technique is cordocentesis or percutaneous umbilical cord blood sampling, commonly known as fetal blood sampling. Fetal blood sampling involves obtaining fetal blood cells from vessels of the umbilical cord, and is performed about the $20^{th}$ gestational week.

Amniocentesis is used selectively because it presents a risk of about 1% of inducing spontaneous abortion. CVS and fetal blood sampling carry a similar or higher risk of inducing abortion, and there is also concern that these procedures may lead to fetal limb malformations in some cases. Thus, amniocentesis, CVS and fetal blood sampling are procedures that are only employed if a pregnancy is considered at high risk for a serious congenital anomaly. Thus, some means is required to select those pregnancies that are at a significant risk of Downs syndrome to justify the risks associated with invasive prenatal diagnostic procedures, such as amniocentesis, CVS and fetal blood sampling.

Prior to 1983, the principal method for selecting pregnancies that had an increased risk for Downs syndrome was based on material age, that is, the older the age of the mother, the higher the risk that the fetus would be affected by Downs syndrome. In 1974, biochemical screening for neural tube defects by measuring alpha-fetoprotein (AFP) in serum began. In 1984, the use of the AFP screen was additionally adopted for the detection of Downs syndrome. Since the early 1990s, a multiple marker blood test has been used to screen for this disorder. A common version of this test is the three marker triple test. The triple screen measures AFP, human chorionic gonadotropin (hCG) and unconjugated estriol ($uE_3$) in the serum of pregnant women.

The triple screen provides a means to screen the population of pregnant women to determine which pregnancies are at risk for Downs syndrome and other serious genetic defects. The risk is calculated based on the results of the screen, along with other cofactors, such as, maternal age, to determine if the risk is high enough to warrant an invasive diagnostic procedure, such as, amniocentesis, CVS or fetal blood sampling. Such prenatal screens, as the triple screen, can be used either to reduce the need for amniocentesis or to increase Downs syndrome detection for the same number of amniocentesis. "The efficiency of the Triple test is projected to be one case of fetal Downs syndrome detected for every 50 amniocenteses performed." Canick and Knight, "Multiple-marker Screening for Fetal Downs Syndrome," Contemporary OB/GYN, pp. 3–12 (April 1992).

Although pregnant women who are 35 years or older are the standard high risk group for fetal Downs Syndrome, screening also needs to be applied to young women because although they are at lower risk, most affected pregnancies are in young women. Approximately 80% of babies born with Downs syndrome are born to mothers under 35. ["Downs Syndrome Screening Suggested for Pregnant Women under 35, ACOG Newsletter, 38(8): 141 (August 1994).]

The triple screen combines the analysis of three serum markers to reduce false positive results (which result in the performance of unnecessary invasive procedures) and false negatives (in which serious genetic defects, such as, trisomy 21, go undetected). In women under 35, the double screen (AFP and hCG) can detect about half of Downs syndrome cases and a large proportion of other chromosome defects during the second trimester. The triple screen (AFP, hCG and $uE_3$) increases the detection rate of Downs syndrome by 5–10% and a further increase in the detection of all other serious chromosome defects, thus decreasing the number of false-negatives. Such rates mean that the double and triple screens still fail to detect a significant number (30%–35%) of Downs syndrome affected pregnancies.

Other screening markers have been found which may offer some predictive value with respect to Downs Syndrome. The present Applicant has added to this repertoire of predictive markers by finding that leptin, prorenin and/or renin are predictive of a pregnancy being affected by Downs Syndrome.

Leptin has heretofore been associated with obesity. Obesity is the result of a disorder in the body energy balance that occurs when energy intake chronically exceeds energy expenditure. This excess in energy intake is stored in the adipocyte. The recently discovered hormone leptin contributes to the regulation of energy balance by informing the brain of the amount of adipose tissue in the body. The brain may then make the appropriate adjustments in either energy intake or expenditure. Leptin is the protein product of the ob gene and in humans is expressed exclusively in adipose tissue. Studies suggest that leptin is a negative regulator of adiposity. However, leptin has only recently been discovered and further investigations into its actions in humans and its role in obesity remain to be determined. Leptin has also heretofore been generally associated with reproductive function. Renin is an enzyme that belongs to the family of aspartyl proteases, a classification that is based on the properties of having 2 aspartic acid residues at the active site and its susceptibility to inhibition by pepstatin. Renin synthesis was first discovered in the juxtaglomerular cells of the kidney. At present there is evidence that renin synthesis can also occur in other organs such as brain, heart and arterial smooth muscle. Renin circulates in two different forms, prorenin and the active renin form. Prorenin is the enzymatically inactive biosynthetic precursor of renin. In the secretory granules of the juxtaglomerular cell, prorenin is processed to active renin by a thiol protease resembling cathepsin B. An amino terminal prosegment of 42 amino acids is cleaved from the prorenin which allows the exposure of the active site of renin. Active renin converts angiotensinogen (renin substrate) to the biologically inactive decapeptide angiotensin I. Angiotensin I in turn is converted to the octapeptide angiotensin 11 by means of the angiotensin converting enzyme (ACE). Angiotensin II causes constriction of the small arteries and also promotes sodium and water reabsorption in tubules both directly and indirectly via aldosterone. Aldosterone is a steroid hormone produced by the adrenal gland and its secretion is stimulated by Angiotensin II. Heretofore, the clinical utility of plasma renin is mainly centered around the diagnosis and management of patients with hypertension due to renal artery stenosis or renovascular hypertension. Approximately 10% of the adult population suffers from hypertension. Renal vascular stenosis is the cause of this hypertension in a subgroup of the patients. This subgroup constitutes 1% of the total hypertensive population. A rise in plasma prorenin often precedes the onset of vascular injury in patients with diabetes mellitus. Plasma prorenin measurements may be useful for predicting which patients will develop vascular injury and for monitoring the progression of the disease. .

Human chorionic gonadotropin (hCG) stimulation of the ovaries leads to elevated serum prorenin levels. Prorenin levels, like hCG, are high during the first trimester of pregnancy and decrease in the 2nd and 3rd trimesters. Since hCG levels are increased in Downs syndrome pregnancies relative to normal pregnancies and hCG stimulation leads to increased prorenin levels, this led Applicant to postulate that prorenin (or renin) may also be increased in Downs Syndrome pregnancies.

Accordingly, it would be desirable to provide assay methods and compositions for leptin and/or prorenin and/or renin which would have predictive value with respect to the likelihood that a pregnant woman is carrying a fetus having Downs Syndrome.

SUMMARY OF THE INVENTION

Leptin levels in maternal biological samples are 3-fold higher during pregnancy and correlate positively with human chorionic gonadotropin (hCG) and progesterone levels. hCG levels are increased in Downs syndrome pregnancies relative to normal pregnancies; these facts provided the impetus to the Applicant to determine if the leptin levels correlation with hCG levels may extend to a relative increase in leptin in Downs Syndrome affected pregnancies.

In one aspect, the presently claimed subject matter is directed to a method of determining an increased risk of a woman carrying a Downs Syndrome affected fetus. The method comprising the steps of: quantitatively assaying a sample from a pregnant woman for an amount of leptin in the sample, thereby determining the amount of leptin in the sample; and comparing the amount of leptin in the sample from the pregnant woman with an amount of leptin found in pregnant women carrying a Downs syndrome unaffected fetus and comparing the amount of leptin in the sample from the pregnant woman with an amount of leptin found in pregnant women carrying a Downs syndrome affected fetus, thereby determining those at an increased risk of carrying a Downs syndrome affected fetus.

In a further aspect of the presently claimed subject matter, the amount of leptin in the sample as determined in a sample from a pregnant woman is below the median amount of leptin found in a pregnant women carrying a Downs syndrome unaffected fetus In one embodiment of the present invention, the sample from the pregnant women is selected from the group consisting of serum, plasma or urine.

In another embodiment of the presently claimed subject matter, the sample is taken from a pregnant women in either of the first trimester or the second trimester or the third trimester of pregnancy.

In a particular embodiment of the presently claimed subject matter, the quantitative assay of the sample is performed by immunoassay, more particularly a competitive immunoassay or a direct immunoassay. In a particular embodiment, a radioimmunoassay can be used.

In another embodiment of the presently claimed subject matter, an additional step of analyzing at least one additional analyte selected from the group consisting of hCG, unconjugated estriol, alpha-fetoprotein, inhibin, PAPP-A, progesterone, DHEA-S or Leukocyte acid phosphatase is performed.

In yet another embodiment, an additional step of analyzing at least one additional factor predictive of an increased risk of a fetus being affected by Downs syndrome is performed. In a preferred embodiment, an ultrasound result is the additional predictive factor.

Human chorionic gonadotropin (hCG) stimulation of the ovaries leads to elevated serum prorenin levels. Prorenin levels, like hCG, are high during the first trimester of pregnancy and decrease in the 2nd and 3rd trimesters. Since hCG levels are increased in Downs syndrome pregnancies relative to normal pregnancies and hCG stimulation leads to increased prorenin levels, this led Applicant to postulate that prorenin (or renin) may also be increased in Downs Syndrome pregnancies.

In another aspect, the presently claimed subject matter is directed to a method of determining an increased risk of a woman carrying a Downs Syndrome affected fetus. The method comprising the steps of: quantitatively assaying a sample from a pregnant woman for an amount of prorenin in the sample, thereby determining the amount of prorenin in the sample; and comparing the amount of prorenin in the sample from the pregnant woman with an amount of prorenin found in pregnant women carrying a Downs syndrome unaffected fetus and comparing the amount of prorenin in the sample from the pregnant woman with an amount of prorenin found in pregnant women carrying a Downs syndrome affected fetus, thereby determining those at an increased risk of carrying a Downs syndrome affected fetus.

In a further aspect of the presently claimed subject matter, the amount of prorenin in the sample as determined in a sample from a pregnant woman is below the median amount of prorenin found in a pregnant women carrying a Downs syndrome unaffected fetus In one embodiment of the present invention, the sample from the pregnant women is selected from the group consisting of serum, plasma or urine.

In another embodiment of the presently claimed subject matter, the sample is taken from a pregnant women in either of the first trimester or the second trimester or the third trimester of pregnancy.

In a particular embodiment of the presently claimed subject matter, the quantitative assay of the sample is performed by immunoassay, more particularly a competitive immunoassay or a direct immunoassay. In a particular embodiment, a radioimmunoassay can be used.

In another embodiment of the presently claimed subject matter, an additional step of analyzing at least one additional analyte selected from the group consisting of hCG, unconjugated estriol, alpha-fetoprotein, inhibin, PAPP-A, progesterone, DHEA-S or Leukocyte acid phosphatase is performed.

In yet another embodiment, an additional step of analyzing at least one additional factor predictive of an increased risk of a fetus being affected by Downs syndrome is performed. In a preferred embodiment, an ultrasound result is the additional predictive factor.

In another aspect, the presently claimed subject matter is directed to a method of determining an increased risk of a woman carrying a Downs Syndrome affected fetus. The method comprising the steps of: quantitatively assaying a sample from a pregnant woman for an amount of renin in the sample, thereby determining the amount of renin in the sample; and comparing the amount of renin in the sample from the pregnant woman with an amount of renin found in pregnant women carrying a Downs syndrome unaffected fetus and comparing the amount of renin in the sample from the pregnant woman with an amount of renin found in pregnant women carrying a Downs syndrome affected fetus, thereby determining those at an increased risk of carrying a Downs syndrome affected fetus.

In still further aspects combinations of leptin and/or prorenin and/or renin are assayed and statistical methods of analyzing the contribution of more than two factors to the likelihood of an outcome, as are known in the art, are used to predict those at an increased risk of carrying a Downs syndrome affected fetus.

Other features and advantages of the invention will become apparent from the following detailed description.

DETAILED DESCRIPTION OF THE INVENTION

A total of 397 second trimester (15–20 weeks gestation) serum samples were collected from individuals with a normal Downs Syndrome risk (<1:270 based on the individual's maternal age, and levels of alpha fetoprotein [AFP], hCG, and unconjugated estriol [uE3]). A total of 10 second trimester serum samples from known Downs Syndrome pregnancies were also collected. All samples were tested blindly for leptin utilizing a radioimmunoassay. It is to be understood that other methods of assay which allow for the quantification of leptin in a biological sample and which are or may become available are within the scope of the present invention.

Lepin values in unaffected pregnancies were both gestational age and maternal age independent. A positive correlation was observed, however, with maternal weight ($R^2$= 0.5345). Results from the unaffected pregnancies ranged from 1.2 to 93.6 ng/ml (median of 19.5 ng/mL, 1.0 (Multiple of the Median ("MoM")). Results from the 10 Downas Syndrome pregnancies ranged from 2.7–44.7 ng/mL (median of 11.7 ng/mL, 0.60 MoM, p=0.012). None of the levels from Downs Syndrome pregnancies exceeded the 95th percentile; however, 2 were below the 5th percentile. Only one exceeded 1.70 multiples of the median (MoM), but levels from 6 of the 10 Downs Syndrome pregnancies were below 0.7 MoM.

The data illustrate that leptin levels are significantly decreased in Downs Syndrome pregnancies relative to unaffected pregnancies. The 0.60 median MoM is lower than that typically reported in the peer reviewed literature for AFP (0.73 MoM) and uE3 (0.72 MoM), but is not quite as large a difference from unaffected pregnancies as in hCG (1.70 MoM). Thus, it appears that leptin is a more sensitive marker for Downs Syndrome risk than AFP and uE3, but not quite as sensitive as hCG.

TABLE 1

Median of leptin concentration in unaffected cases

| Gestational Age (weeks) | n | Median (ng/mL) |
|---|---|---|
| 15 | 68 | 17.4 |
| 16 | 60 | 19.4 |
| 17 | 71 | 19.2 |
| 18 | 60 | 24.1 |
| 19 | 69 | 17.6 |
| 20 | 68 | 23.6 |
| All weeks | 397 | 19.5 |

TABLE 2

Leptin MoM in Downs syndrome affected and unaffected cases

| Affected Cases | MoM | Affected cases (ng/mL) |
|---|---|---|
| 1 | 0.14 | 2.7 |
| 2 | 0.35 | 6.9 |
| 3 | 0.45 | 8.7 |
| 4 | 0.51 | 9.9 |
| 5 | 0.56 | 11.0 |
| 6 | 0.64 | 12.4 |
| 7 | 0.74 | 14.4 |
| 8 | 0.77 | 15.1 |
| 9 | 1.11 | 21.6 |
| 10 | 2.29 | 44.7 |
| Mean | 0.76 | |
| Median | 0.60 | Unaffected - 1.00 |

EXAMPLE 1

Leptin Assay

In a particular embodiment of the claimed method, leptin can be quantitated with the RIA Kit, available from Linco Research, Inc. 14 Research Park Drive, St. Louis Mo. 63304. The Linco RIA Kit provides for a competition assay format for assaying for leptin. However, direct immunoassays and other quantitative assay methods as are known in the art or as will be developed are within the scope of the present claims. The standards, Quality Control ("QC") pools, and samples are incubated with the highly specific Rabbit anti-human Leptin in assay buffer and radiolabeled $^{125I-}$leptin in an equilibrium radioimmunoassay. The assay buffer is, for example, 0.05 M Phosphosaline at pH 7.4, with 0.025M EDTA, 0.1% Sodium azide, 1% RIA grade BSA and 0.05% Triton X-100.

The bound/free separation is achieved with the Precipitating Reagent, for example, a Goat anti Rabbit IgG serum in 3%PEG and 0.05% Triton X-100 in 0.05 M Phosphosalline, 0.025 M EDTA, 0.1% sodium azide and centrifugation. The resulting antibody-bound radiolabeled $^{125I-}$leptin is measure in a gamma counter and the raw data (cpm's) are data reduced, preferably, by a computer program, as would be known to those of ordinary skill in the art, that constructs a standard curve using a dose-response relationship from which the QC pools and samples are read from.

The disclosure herein describes the basic process of data reduction which may be performed manually on raw data. Counted data may also be reduced in part or in whole with assistance of programmable counting equipment or computer processing.

Assay Parameters:

Non-specific binding (NSB)

$$\% NSB = \frac{CPM(NSB)}{CPM(TC)} \times 100$$

TC=Total Counts
NSB=Non-specific binding
Maximum Binding (Bmax)

$$\% Bmax = \frac{CPM(Bo) - CPM(NSB)}{CPM(TC)} \times 100$$

Bmax=maximum binding
Bo=binding in the zero standard (tubes 5 & 6)
Dose-response variables:
Percent bound for the standards, controls, and specimens, also known as the response.
B=binding for standards, controls, and specimens.
A dose-response curve (DRC) can be constructed using a log-logit transformation of standard dose (concentration) versus % B/Bmax.
Typical Values for adults (18–61 years) who are Lean Subjects with BMI range of 18–25 are as follows:
Adults Males 1.2–9.5 ng/mL (n=59).
Adult Females 4.1–25.0 ng/mL (n=60).
BMI=Body Mass Index=Body weight in Kilograms= $(Kg/M^2)$; Height in Meter$^2$ The control and sample results can be reported to the nearest tenth of a decimal in ng/mL of leptin. The following reference is incorporated herein by reference: Zhongmin, Ma., Gingerich, R. L., et. al. Radioimmunoassay of Leptin in Human Plasma. Clinical Chemistry. 42;6: 942–946, 1996.

The most preferred maternal biological sample type is serum, however, plasma is also acceptable. Other biological samples which may be used include, urine, saliva, ascites fluid, peritoneal fluid and other biological fluids.

A total of 418 second trimester (15–20 weeks gestation) serum samples were collected from individuals with a normal Downs Syndrome risk (<1:270 based on the individual's maternal age, and the levels of alpha fetoprotein [AFP], hCG, and unconjugated estriol [uE$_3$]). A total of 10 second trimester serum samples from known Downs Syndrome pregnancies were also collected. All samples were tested blindly for prorenin, and total renin in an immunoradiometric assay.

Prorenin and renin levels in unaffected pregnancies were gestational age (GA) independent; however, total renin levels were slightly GA dependent (levels decreased with increasing GA). All three analytes were maternal age independent. The following medians set forth in Table 3 were obtained in unaffected and Downs Syndrome pregnancies:

|  | Unaffected Pregnancies | | Affected Pregnancies | |
| --- | --- | --- | --- | --- |
|  | mU/L | MoM | mU/L | MoM |
| Prorenin medians | 641 | 1.0 | 440 | 0.69 |
| Renin medians | 182 | 1.0 | 310 | 1.71 |
| Total renin medians | 824 | 1.0 | 929 | 1.15 |

TABLE 4

Median Prorenin concentration in unaffected cases

| Gestational Age (weeks) | n | Median (mU/L) |
| --- | --- | --- |
| 15 | 68 | 746 |
| 16 | 73 | 720 |
| 17 | 63 | 632 |
| 18 | 75 | 578 |
| 19 | 75 | 647 |
| 20 | 64 | 582 |
| All weeks | 418 | 641 |

TABLE 5

Prorenin MoM in downs Syndrome affected and unaffected cases

| Affected Cases | MoM | Affected (mU/L) |
| --- | --- | --- |
| 1 | 0.05 | 33 |
| 2 | 0.42 | 271 |
| 3 | 0.51 | 328 |
| 4 | 0.54 | 347 |
| 5 | 0.61 | 392 |
| 6 | 0.76 | 488 |
| 7 | 0.82 | 528 |
| 8 | 0.96 | 615 |
| 9 | 1.17 | 753 |
| 10 | 1.30 | 834 |
| Mean | 0.71 |  |
| Median | 0.69 | Unaffected 1.00 |

TABLE 6

Median of Renin concentration in downs syndrome unaffected cases

| Gestational Age (weeks) | n | Median (mU/L) |
| --- | --- | --- |
| 15 | 67 | 204 |
| 16 | 74 | 187 |
| 17 | 63 | 188 |
| 18 | 74 | 148 |
| 19 | 79 | 172 |
| 20 | 63 | 183 |
| All weeks | 420 | 180 |

TABLE 7

Renin MoM in Downs syndrome affected and unaffected cases

| Affected Cases | MoM | Affected (mU/L) |
| --- | --- | --- |
| 1 | 0.60 | 113 |
| 2 | 4.35 | 748 |
| 3 | 1.44 | 248 |
| 4 | 1.31 | 225 |
| 5 | 0.68 | 125 |
| 6 | 1.94 | 396 |
| 7 | 1.41 | 265 |
| 8 | 4.01 | 819 |
| 9 | 4.21 | 858 |

TABLE 7-continued

Renin MoM in Downs syndrome affected and unaffected cases

| Affected Cases | MoM | Affected (mU/L) |
|---|---|---|
| 10 | 1.74 | 355 |
| Mean | 2.41 | |
| | | Unaffected Median 1.00 |

Prorenin levels are significantly decreased in Downs Syndrome pregnancies (p=0.23), where as renin concentrations are increased. The 0.69 and 1.71 median MoMs for prorenin and renin are similar to the MoMs of current prenatal screening markers (0.73 MoM for AFP, 1.70 MoM for hCG, and 0.72 for uE3). Based on this finding, prorenin appear to be useful markers for prenatal Downs Syndrome screening.

The data presented above for leptin and prorenin/renin is given in values of ng/mL and mU/L respectively. However, by the terms "amount of leptin" or "amount of prorenin" or "amount of renin" is meant any information regarding, for example, either the amount of an analyte present, e.g., in units such as mols, or the weight of an analyte present such as in mg, either of which may be further characterized in relation to their presence per unit volume or weight of a liquid. However, any units and any physical characteristics which allow for the medically or biochemically relevant comparison of different samples with respect to leptin and/or prorenin and/or renin are within the cope of the present invention and the terms "amount of leptin" or "amount of prorenin" "amount of direct renin".

additionally, the terms "amount of leptin" or "amount of prorenin" or "amount of direct renin" includes values provided by indirect measurements of leptin and/or prorenin and/or renin, such as, chemiluminescent, fluorescent, electrical, chemical or otherwise machine or human detectable signals which either provide medically or biochemically relevant information or which can be mathematically manipulated to provide the "amount of leptin" or "amount of prorenin" or "amount of renin" as those terms are defined in the preceding paragraph. Similarly, the use of statistical measurements such as the median can be replaced with other statistical measures as are known in the art. Also, by the term "quantitatively assay" is meant obtaining an actual value for one of leptin or prorenin or use of a means which has a predetermined sensitivity for a given amount of leptin or renin or prorenin. For example, use of a dipstick that gives a human readable signal only when an analyte is above or below a given threshold.

The methods of the present invention can be used in all types of assays, for example, direct, competitive, simultaneous, sequential and sandwich assays as are known in the art are within the scope of the present claims.

EXAMPLE 2

Prorenin and Renin Assay

Renin, Prorenin, and Total Renin are measured by, for example, the Nichols Institute Diagnostics, 33051 Calle Aviador, San Juan Capistrano, Calif. 92675, BV Active Renin Assay which is a two site radioimmunometric assay (IRMA) utilizing two different monoclonal antibodies to human Renin. One monoclonal antibody is coupled to biotin, while the other monoclonal antibody is radiolabeled, with for example $^{125}$I, for detection. Renin is "sandwiched" between these two antibodies and this complex is bound to a solid phase avidin coated bead via the high affinity interaction between the biotin and avidin. Lyophilized Standards containing human active renin in sheep serum with 0.1% sodium azide as a preservative can be used. These standards are calibrated by the manufacturer against the World Health Organizations 2nd IRP (68/356) for actual renin. One (1) m U/L obtained using the Active Renin Assay is equivalent to 0.6 pg/mL of WHO $2^{nd}$ IRP (68/356) for active Renin.

After incubation, the bead is washed to remove unbound components and the radioactivity bound to the solid phase is measured in a gamma counter. The radioactivity of the bound sandwich complex is directly proportional to the amount of immunoreactive renin in the sample. Total Renin is quantitated by adding a Renin "Inhibitor" to the sample which causes the non-immunoreactive prorenin to become immunoreactive and thus a Total Renin measurement (renin+prorenin) is achieved. Prorenin is therefore calculated by subtracting the Renin measurement from the Total Renin measurement of the sample. The resulting difference is the Prorenin quantitation. Total Renin—Renin=Prorenin A representative dose curve (RDRC) can be prepared by calculating the mean and ±2 SD of the cpm for each point of the standard curve in at least 10 acceptable assays.

The disclosure herein describes the basic process of data reduction which may be performed manually on raw data. Counted data may also be reduced in part or in whole with assistance of programmable counting equipment or computer processing.

The CPM of each standard dose replicate is plotted against the standard dose concentration (Linear vs. Linear). A computer program draws a smooth point to point curve using a Spline Curve Fitting reduction. Sample doses are read off the Spline Dose Response Curve (DRC) for each CPM replicate. The computer then averages the read doses (duplicate) and calculates the mean dose and % CV. Control and Sample values are averaged to the nearest whole number. Prorenin measurements are calculated by subtracting the Renin from the Total Renin measurements.

Normal Values for adults are as follows:

| Renin: | 12–79 mU/L | Supine Adult |
|---|---|---|
| | 13–114 mU/L | Upright Adult |
| Prorenin: | 57–285 mU/L | 21–35 Years |
| | 48–224 mU/L | >36 Years |
| Total Renin: | 64–325 mU/L | Adults |

The following references are incorporated herein by reference: Hsueh W A and Baxter J D. Human prorenin. Hypertension 1991; 17:469; Derkx FHM, Stuenkel C, Schalekamp MPA, Visser W, Huisveld I H and Schalekamp MADH. Immunoreactive renin, prorenin and enzymatically active renin in plasma during pregnancy and in women taking oral contraceptives. J. Clin. Endocrinol. Metab. 1986; 63:1008; Sealey J E. Plasma Renin Activity and Plasma Prorenin Assays. Clin. Chem. 1991:37/10(B), 1811–1819; Heusser C H, Bews J P A, Alkan S S, Dietrich F M, Wood J M, de Gasparo M, and Hofbauer K G. Monoclonal antibodies to human renin: properties and applications. Clin. Exper. Theory Practice 1987; A9(8&9):1259-1275; Zuo W M, Pratt R E, Heusser C H, Bews J P A, de Gasparo M, and Dzau V J. Characterization of a monoclonal antibody specific for human active renin. Hypertension 1992; 19:249–254; Simon D, Hartmann D J, Badouaille G, Caillot G, Guyenne T T, Corvol P, Pau B, Marchand J. Two-Site direct Immunoassay Specific for Active Renin. Clin. Chem. 1992;38/10, 1959–1962; Rodbard, D., and Hutt, D.: Statistical Analysis of Radioimmunoassays and Immunoradiometric (labeled antibody) Assay. Radioimmunoassays and Related Procedures in Medicine. Vol. 1, Vienna: International Atomic Energy Agency, Vienna, 1974.

The most preferred biological sample type is serum, however, plasma is also acceptable. Other biological samples which may be used include, urine, saliva, ascites fluid, peritoneal fluid and other biological fluids.

The presently disclosed embodiments are to be considered in all respects as illustrative and not restrictive, the scope of the invention being indicated by the appended claims, rather than the foregoing description, -and all changes which come within the meaning and range of equivalency of the claims are therefore intended to be embraced therein.

What is claimed is:

1. A method of determining an increased risk of a woman carrying a Downs Syndrome affected fetus, the method comprising the steps of:
   a) quantitatively assaying a sample from a pregnant woman for an amount of prorenin in the sample, thereby determining the amount of prorenin in the sample; and
   b) comparing the amount of prorenin in the sample in step a with an amount of prorenin found in pregnant women carrying a Downs syndrome unaffected fetus and comparing the amount of prorenin in the sample in step a with an amount of prorenin found in pregnant women carrying a Downs syndrome affected fetus, thereby determining those at an increased risk of carrying a Downs syndrome affected fetus.

2. The method of claim 1 wherein the amount of prorenin in the sample as determined in step a is below the median amount of prorenin found in a pregnant women carrying a Downs syndrome unaffected fetus.

3. The method of claim 1 wherein the sample from the pregnant women is selected from the group consisting of serum, plasma or urine.

4. The method of claim 1 wherein the sample is taken from a pregnant women in either of the first trimester or the second trimester or the third trimester of pregnancy.

5. The method of claim 1 wherein the quantitative assay of the sample is performed by immunoassay.

6. The method of claim 1 further comprising the step of analyzing at least one additional analyte predictive of an increased risk of a fetus being affected by Downs syndrome.

7. A method of determining an increased risk of a woman carrying a Downs Syndrome affected fetus, the method comprising the steps of:
   a) quantitatively assaying a sample from a pregnant woman for an amount of renin in the sample, thereby determining the amount of renin in the sample; and
   b) comparing the amount of renin in the sample in step a with an amount of renin found in pregnant women carrying a Downs syndrome unaffected fetus and comparing the amount of renin in the sample in step a with an amount of renin found in pregnant women carrying a Downs syndrome affected fetus, thereby determining those at an increased risk of carrying a Downs syndrome affected fetus.

8. The method of claim 7 wherein the amount of renin in the sample as determined in step a is below the median amount of renin found in a pregnant women carrying a Downs syndrome unaffected fetus.

9. The method of claim 7 wherein the sample from the pregnant women is selected from the group consisting of serum, plasma or urine.

10. The method of claim 7 wherein the sample is taken from a pregnant women in either of the first trimester or the second trimester or the third trimester of pregnancy.

11. The method of claim 7 wherein the quantitative assay of the sample is performed by immunoassay.

12. A method of determining whether there is an increased risk of a woman carrying a fetus which is affected by Downs Syndrome, the method comprising the steps of:
   b) quantitatively assaying a sample from a pregnant woman for an amount of renin in the sample, thereby determining the amount of renin in the sample;
   b) comparing the amount of renin in the sample in step a with an amount of renin found in pregnant women carrying a Downs syndrome unaffected fetus and comparing the amount of renin in the sample in step a with an amount of renin found in pregnant women carrying a Downs syndrome affected fetus,
   c) quantitatively assaying a sample from a pregnant woman for an amount of prorenin in the sample, thereby determining the amount of prorenin in the sample; and
   d) comparing the amount of prorenin in the sample in step a with an amount of prorenin found in pregnant women carrying a Downs syndrome unaffected fetus and comparing the amount of prorenin in the sample in step a with an amount of prorenin found in pregnant women carrying a Downs syndrome affected fetus, thereby determining those at an increased risk of carrying a Downs syndrome affected fetus.

13. The method of claim 12 wherein the sample from the pregnant women is selected from the group consisting of serum, plasma or urine.

14. The method of claim 12 wherein the sample is taken from a pregnant women in either of the first trimester or the second trimester or the third trimester of pregnancy.

15. The method of claim 12 wherein the quantitative assay of the sample is performed by immunoassay.

16. The method of claim 12 further comprising the step of analyzing at least one additional analyte predictive of an increased risk of a fetus being affected by Downs syndrome.

* * * * *